United States Patent [19]

Martin

[11] 4,220,464
[45] Sep. 2, 1980

[54] PHENYLGLYOXYLONITRILE-2-OXIME-CYANOMETHYL ETHER AS PLANT GROWTH REGULATOR

[75] Inventor: Henry Martin, Allschwil, Switzerland

[73] Assignee: CIBA-GEIGY Corporation, Ardsley, N.Y.

[21] Appl. No.: 938,210

[22] Filed: Aug. 30, 1978

Related U.S. Application Data

[63] Continuation-in-part of Ser. No. 772,700, Feb. 28, 1977, Pat. No. 4,152,137, which is a continuation-in-part of Ser. No. 717,792, Aug. 25, 1976, Pat. No. 4,070,389.

[30] Foreign Application Priority Data

Sep. 4, 1975 [CH] Switzerland ............... 11458/75

[51] Int. Cl.$^2$ ............................................. A01N 21/02
[52] U.S. Cl. ................................................ 71/77
[58] Field of Search .................................. 71/77, 105

[56] References Cited

U.S. PATENT DOCUMENTS

| | | | |
|---|---|---|---|
| 3,483,246 | 12/1969 | Kaufman | 71/105 |
| 3,515,536 | 6/1970 | Hill et al. | 71/77 |
| 3,799,757 | 3/1974 | Dixon et al. | 71/105 |
| 3,907,861 | 9/1975 | Puttner et al. | 71/105 |
| 4,063,921 | 12/1977 | Hubele et al. | 71/105 |

Primary Examiner—Glennon H. Hollrah
Attorney, Agent, or Firm—Frederick H. Rabin

[57] ABSTRACT

Phenylglyoxylonitrile-2-oxime-cyanomethyl ether of the formula

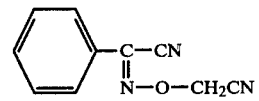

and compositions containing it, have various advantageous effects with regard to regulation of plant growth. Furthermore, this compound and its compositions have the property of rendering, in the sense of an antidote (safening) action, agricultural chemicals which would otherwise damage the plants more compatible with cultivated plants. Strong herbicides, for example chloroacetanilides or thiolcarbamates, can be used in the presence of such safening agents in specific crops such as sorghum and rice for combatting weeds without disadvantageous consequences for the crops. The safeners are preferably applied to the crop seeds prior to planting.

5 Claims, No Drawings

PHENYLGLYOXYLONITRILE-2-OXIME-CYANOMETHYL ETHER AS PLANT GROWTH REGULATOR

CROSS REFERENCE TO RELATED APPLICATIONS

This is a continuation-in-part of my application Ser. No. 772,700, filed FEB. 28, 1977, now U.S. Pat. No. 4,152,137, which is in turn a continuation-in-part of my application Ser. No. 717,792, filed Aug. 25, 1976, now U.S. Pat No. 4,070,389.

BACKGROUND OF THE INVENTION

The present invention relates to a novel oxime ether and to compositions containing this oxime ether, and to the use of this compound of these compositions as plant growth regulators or, optionally together with a herbicide, to its use as antidotes (safeners) for herbicides, which damage certain cultivated plants, so that such herbicides can be employed as selective herbicides, without loss of their herbicidal action against weeds, in crops of these cultivated plants.

The oxime ether of this invention has extraordinarily advantageous properties for regulating plant growth, without there being any disadvantageous consequences for the plants treated therewith. Applied in small dosage amounts, this compound has in particular the ability to stimulate both the germinating seed and the young plants which are developing. With specific dosage amounts, this leads to a clearly enlarged root system, to an incresed rate of photosynthesis and to a more rapid development of parts of plants above the soil. The action of the oxim is however not restricted to the early stage of plant development, but can be observed also in the case of later application, or in the case of a partial application to specific parts of plants (seed dressings, pre-swelling of the seed, root treatment, treatment of shoots or leaf application).

Another advantageous property is the possibility, even under environmental conditions that are not particularly favourable, of achieving a satisfactory development of the crop of cultivated plants and thus an adequate crop yield.

The oxime ether of this invention possesses thus to a very great extent properties for regulating plant growth, depending on the point of time of application, on the type of plant and on the conditions of application that may vary in a wide range.

Compositions for influencing plant growth, especially for inhibiting growth, have already been described at various times; thus, chlorocholine chloride in particular is suitable for the shortening and stabilising of the stems in wheat crops. According to German Offenlegungsschrift No. 2,458,165, bis-(p-chlorophenyl)-acetic acid, or salts, esters amides or nitriles thereof, are said to effect a similar shortening of stems in cereal crops. In German Offenlegungsschrift No. 2,407,148, 2,6-disubstituted phenoxyacetates or 2,6-disubstituted phenoxypropionates are recommended as growth regulators. The mode of acting of these substances, particularly with low applied amounts and low concentrations, is however not satisfactory. The position is similar in the case of p-chlorophenyl-dimethylacetic acid (East German Patent Specification No. 113,890), and also in the case of 2-cyano-bicyclo[2,2,1]heptane (French Patent Specification No. 2,256,722). As was shown by tests, the action of these compounds is very unsatisfactory.

The arylglyoxilnitrile oximes, suggested in the U.S. Patent Specification No. 3,799,757, of the general formula

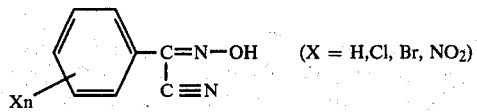     (X = H,Cl, Br, NO₂)

are insufficiently effective as growth inhibitors and plant-growth regulators; they are moreover not stable and decompose after a fairly short period of time.

The oxime of the invention surprisingly possesses a further very important property. It is excellently suitable for protecting cultivated plants, such as cultivated millet, rice, maize, varieties of cereals (wheat, rye, barley or oats), cotton, sugar beet, sugar cane, soya bean, etc., against being attacked by agricultural chemicals, particularly by herbicides of the widest variety of classes of substances, such as triazines, phenylurea derivatives, carbamates, thiolcarbamates, halogenoacetanilides, halogenophenoxyacetates, substituted phenoxyphenoxyacetates and -propionates, substituted pyridineoxyphenoxyacetates and -propionates, benzoic acid derivatives, etc., in cases where these do not act selectively or not sufficiently selectively, that is to say, damage to a greater or lesser extent the cultivated plants in addition to the weeds to be combated.

Various substances have already been suggested for overcoming this problem, which substances are able to specifically antagonise the harmful action of a herbicide on the cultivated plant, i.e. to protect the cultivated plant without noticeably affecting the herbicidal action on the weeds to be combated. Depending on its properties, such an antidote can be used for the preliminary treatment of the seed of the cultivated plant (dressing of the seed or of the seedlings); or it can be applied into the seed furrows before sowing; or it can be applied as a tank mixture, on its own or together with the herbicide, before or after emergence of the plants. The treatment with the antidote can be carried out before or after, or simultaneously with, the herbicidal treatment. The pre-emergence treatment includes both the treatment of the cultivated area before sowing (ppi=pre plant incorporation) and the treatment of the sown cultivated area before emergence of the plants.

Antidotes frequently have an action that is very specific to the species with regard to the cultivated plants and with regard to the type of active substance of the herbicide (triazines, carbamates, etc.) and often also with regard to the type of application (seed dressing, pre-emergence tank application, etc.); i.e. a specific antidote is frequently suitable only for a specific cultivated plant and for certain herbicidal classes of active substance.

Thus, the British Patent Specification No. 1,277,557 describes the treatment of seed and seedlings of wheat and sorghum with cerain esters and amides of oxamic acid before the attack by N-methoxymethyl-2',6'-diethyl-chloroacetanilide (Alachlor). Other publications (German Offenlegungsschriften Nos. 1,952,910 and 2,245,471, and French Patent Specification No. 2,021,611) suggest antidotes for the treatment of cereals, maize seed and rice seed to protect them against the attack from herbicidal thiolcarbamates. In German Patent Specification No. 1,576,676 and U.S. Pat. No. 3,131,509, hydroxyamino-acetanilides and hydantoins are suggested for protecting cereal seeds against carbamates, such as IPC, CIPC, etc.

In U.S. Pat. Nos. 3,996,043 and 3,998,621, there are described certain antidotes for use with triazine herbicides which permit the herbicides to be used in cotton cultures.

The direct treatment of certain useful plants before or after emergence of the plants on a cultivated area with antidotes as antagonists of specific classes of herbicides is described in German Offenlegungsschriften Nos. 2,141,586 and 2,218,097 and in U.S. Pat. No. 3,867,444.

Whilst maize plants can be excellently protected from damage that can result from strongly herbicidally effective chloroacetanilides, such as have been described in German Offenlegungsschriften Nos. 2,212,268, 2,305,495 and 2,328,340, by an N-substituted dichloroacetamide being applied as antidote to the soil (German Offenlegungsschrift No. 2,402,983), corresponding tests in other crops, such as cultivated millet and rice, have been unsuccessful.

It is therefore among the objects of this invention to provide an antidote (safener) compound which will permit the use of chloroacetanilide herbicides, and other effective weed killers in cultivated crops, particularly sorghum and rice.

It is a further object to provide compositions which contain the antidote (safener) compound, optionally together with biologically active substances, such as herbicides, fungicides, insecticides and the like.

Another object is to provide methods for regulating plant growth by applying to the plants or generative plant parts to be treated the oxime ether of this invention or compositions containing said oxime ether.

Other objects will become apparent from the description of the invention.

There has not hitherto been suggested in the literature a substance which on the one hand is able to impart to plants growth-regulating impulses, and on the other hand has the ability to protect, in the sense of an antidote effect, plants against agressive agricultural chemicals.

SUMMARY OF THE INVENTION

It has now been found that the novel oxime ether of formula I

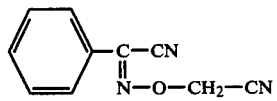

(I)

which can be designated as [O-(cyanomethyl)-oximino]-benzyl-cyanide as [O-(cyanomethyl)-oximino]-αacyanotoluene, or as phenylglyoxylonitrile-2-oximexyanomethyl ether, is excellently suitable for the protection of cultivated plants, such as maize, varieties of cereals (wheat, rye, barley, oats, etc.), cotton, sugar beet, sugar cane, soybean, etc., especially however cultivated millet of the sorghum genus, such as S. vulgare and S. hybridum, as well as rice, from the attack of herbicides of the most varied classes of substances, such as triazines, phenylureas, carbamates, benzoic acid derivates, halogenophenoxyacetic acids, etc., particularly however from the attack of herbicidal halogenoacetanilides and thiolcarbamates.

It has further been found that the oxime ether of formula I is also very suitable for regulating plant growth, in particular of rice and of cultivated millet of the sorghum variety.

DETAILED DISCLOSURE

The free phenylglyoxylonitrile-2-oxime from which the above ether derives and some ring-substituted derivatives of the free oxime are described in U.S. Pat. No. 3,799,757 as growth inhibitors for regulating the growth in height of maize, cereals and soybeans, i.e. for a completely different field of application.

The novel oxime ether of formula I is produced according to the invention by reaction of a salt, especially an alkali metal salt, of phenylglyoxynitrile-2-oxime of formula II

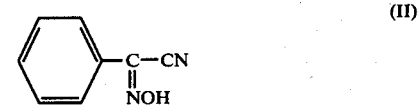

(II)

with a cyanomethyl halide (halogenoacetonitrile) of the formula Hal—CH$_2$-CN.

The starting oxime of formula II is known and can be produced, for example, according to *Organic reactions* 7, pp.343 and 373 (1953). It is known that oximes can exist in two stereoisomeri forms, the syn- and anti-form. Also the oxime ether of formula I according to the invention can exist in both forms and as a mixture thereof. Accordingly, within the scope of the present description are meant both stereoisomeric forms either separately or as a mixture in any reciprocal mixture ratio.

The following Example illustrates the production of the novel oxime ether of formula I.

EXAMPLE I PREPARATION OF ANTIDOTE COMPOUND 33.8 g of phenylglyoxylonitrile-2-oxime (sodium salt) is suspended in 200 ml of acetonitrile in a 350 ml sulphonating flask. An addition is then made dropwise of 15.1 g of chloroacetonitrile in 20 ml of acetonitrile, whereupon a very slight increase in temperature can be observed. The suspension is subsequently refluxed with stirring for 3 hours, during the process of which the reaction mixture assumes a light-green colour. After cooling to room temperature, the formed sodium chloride is filtered off with suction, and the filtrate is concentrated in a rotary evaporator to obtain as residue 31 g of crude product. This is dissolved in 200 ml of acetonitrile; the solution is stirred with charcoal and filtered until clear. Concentration of the filtrate in the rotary evaporator yields 25.4 g of oxime ether (68.6% of theory), m.p. 53–54° C.

Recrystallised from isopropanol, the pure phenylglyoxylonitrile-2-oxime-cyanomethyl ether melts at 56–57° C. (syn-form) The other stereoisomeric form (anti) of this ether melts at 58–59° C. and has a boiling point of 136°C/0.05 torr.

Effective chloroacetanilides, which in some cases are not sufficiently tolerated by cultivated plants, such as cereals, rice, cultivated sorghum, and so forth, but which, when acting together with the oxime ether of the formula I of the present invention, leave such cultivated plants unharmed, without losing any of their normal effectiveness against weeds, have become known, for example, from the U.S. Pat. Nos. 3,547,620, 3,403,994, 3,442,945, 3,637,847, 3,598,859, 3,819,661, 3,946,045 and 3,983,174, and from the German Offenlegungsschriften Nos. 2,212,268, 2,305,495, 2,328,340, 2,402,983, 2,405,183 and 2,405,479. The antidote according to the invention is e.g. used together with herbicidal chloroacetanilides which correspond to the formula III

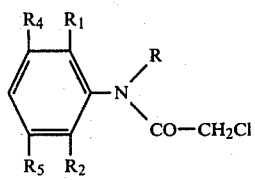

wherein $R_1$ is lower alkyl, alkoxy, alkoxyalkyl, trifluoromethyl or halogen, and $R_2$, $R_4$ and $R_5$ independently of one another are hydrogen, lower alkyl, alkoxy, alkoxyalkyl, trifluoromethyl or halogen, and R is alkyl having 1 to 4 carbon atoms which may be substituted by carboxy, carboxylic acid ester, carboxylic acid amide, carboxylic acid (mono- or di-lower aliphatic) amide or cyano; or wherein R is propynyl, butynyl, acetalized carbonylalkyl, 1,3-dioxolan-2-yl-alkyl, 1,3-dioxolan-5yl-alkyl, 1,3-dioxan-2-yl-alkyl, furanylmethyl, tetrahydrofuranyl methyl or alkoxyalkyl of the formula —A—O—$R_3$, in which A is alkylene having 1 to 4 carbon atoms of which 1 or 2 are in the direct chain, and $R_3$ is lower alkyl or alkenyl or cycloalkyl or cycloalkylmethyl having 3 to 6 ring carbon atoms.

As used herein, the term "lower" as applied to alkyl groups and other hydrocarbon groups refers to groups having up to four carbon atoms. These include, in the case of lower alkyl, methyl, ethyl, n-propyl, isopropyl, n-butyl, isobutyl, sec. butyl and tert. butyl. By "halogen" is meant fluorine, chlorine, bromine and iodine, particularly fluorine and chlorine.

One of the groups of herbicidal chloroacetanilides preferably used are those where in the above formula III $R_1$ is alkyl having 1 to 4 carbon atoms, $R_2$ is alkyl having 1 to 4 carbon atoms, R is alkyl having 1 to 4 carbon atoms which is substituted by carboxylic acid ester, or alkoxyalkyl of the formula —A—O—$R_3$, wherein A is alkylene having 2 or 3 carbon atoms of which 1 or 2 direct chain, $R_3$ is alkyl having 1 to 4 carbon atoms or alkenyl having 2 to 4 carbon atoms, and $R_4$ and $R_5$ are hydrogen.

Some herbicidal chloroacetanilides which are particularly suitable for use with the antidote according to the invention are listed below:

N-ethoxymethyl-2-methyl-6-ethyl-chloroacetanilide,
N-methoxymethyl-2,6-diethyl-chloroacetanilide,
N-(2'-methoxyethyl)-2,6-dimethyl-chloroacetanilide,
N-(2'-allyloxyethyl)-2,6-dimethyl-chloroacetanilide,
N-(2'n-propoxyethyl)-2,6-dimethyl-chloroacetanilide,
N-(2'-isopropoxyethyl)-2,6-dimethyl-chloroacetanilide,
N-(2'-methoxyethyl)-2-methyl-6-ethyl-chloroacetanilide,
N-(2'-methoxyethyl)-2,6-diethyl-chloroacetanilide,
N-(2'-ethoxyethyl)-2-methyl-6-ethyl-chloroacetanilide,
N-(1'-ethoxycarbonyl-ethyl)-2,6-dimethyl-chloroacetanilide,
N-[3'-methoxyprop-(2')-yl]-2-methyl-chloroacetanilide,
N-[3'-methoxyprop-(2')-yl]-2,6-dimethyl-chloroacetanilide,
N-[3'-methoxyprop-(2')-yl]-2-methyl-6-ethyl-chloroacetanilide,
N-[3'-methoxyprop-(2')-yl]-2,6-diethyl-chloroacetanilide,
N-[3'-methoxyprop-(2')-yl]-2-ethyl-chloroacetanilide,
N-(2'-ethoxyethyl)-2,6-diethyl-chloroacetanilide,
N-(2'-n-propoxyethyl)-2-methyl-6-ethyl-chloroacetanilide,
N-(2'-n-propoxyethyl)-2,6-diethyl-chloroacetanilide,
N-(2'-isopropoxyethyl)-2-methyl-6-ethyl-chloroacetanilide,
N-chloroacetyl-2,6-dimethylanilino-acetic acid ethyl ester,
N-chloroacetyl-2,6-diethylanilino-acetic acid ethyl ester,
N-chloroacetyl-2,6-dimethylanilino-acetic acid methyl ester,
N-chloroacetyl-2-methyl-6-ethylanilino-acetic acid isopropyl ester,
β-(N-chloroacetyl-2,6-dimethylanilino)-propionic acid methyl ester,
α-(N-chloroacetyl-2-methyl-6-ethylanilino)-propionic acid ethyl ester
2-[N-(α-chloroacetyl)-2,6-dimethylanilino]acetaldehyde-diethylacetal
N-[3'-methoxyprop-(2')-yl]-2,3-dimethyl-chloroacetanilide,
N-(2'-ethoxyethyl)-2-methyl-chloroacetanilide,
N-(2'-methoxyethyl)-2-methyl-chloroacetanilide,
N-[2'-methoxyprop-(1')-yl]-2,6-dimethyl-chloroacetanilide,
N-[2'-methoxyprop-(1')-yl]-2-methyl-6-ethyl-chloroacetanilide,
N-[3'-ethoxyprop-(2')-yl]-2-methyl-6-ethyl-chloroacetanilide,
N-(2'-ethoxyethyl)-2-fluoro-chloroacetanilide,
N-[3'-ethoxyprop-(2')-yl]-2-fluoro-chloroacetanilide,
N-[1'-methoxybut-(2')-yl]-2,6-dimethyl-chloroacetanilide,
N-(2'-methoxyethyl)-2-methyl-6-methoxy-chloroacetanilide,
N-(n-butoxymethyl)-2-tert.butyl-chloroacetanilide,
N-[3'-ethoxyprop-(2')-yl]-2,6-dimethyl-chloroacetanilide,
N-(2'-methoxyethyl)-2-chloro-6-methyl-chloroacetanilide,
N-(2'-ethoxyethyl)-2-chloro-6-methyl-chloroacetanilide,
N-(2'-ethoxyethyl)-2,3,6-trimethyl-chloroacetanilide,
N-(2'-methoxyethyl)-2,3,6-trimethyl-chloroacetanilide,
N-(2'-isopropoxyethyl)-2,3,6-trimethyl-chloroacetanilide,
N-cyanomethyl-2,6-dimethyl-chloroacetanilide,
N-(but-1-yn-3-yl)-chloroacetanilide,
N-propynyl-2-methyl-6-ethyl-chloroacetanilide,
N-(1,3-dioxolan-2-ylmethyl)-2,6-dimethyl-chloroacetanilide,
N-(1,3-dioxolan-2-ylmethyl)-2-ethyl-6-methyl-chloroacetanilide,
N-(1,3-dioxan-2-ylmethyl)-2-methyl-6-ethyl-chloroacetanilide,
N-(2'-furanyl-methyl)-2,6-dimethyl-chloroacetanilide,
N-(2'-furanyl-methyl)-2-chloro-6-methyl-chloroacetanilide, N-(2'-tetrahydrofuranyl-methyl)-2,6-dimethyl-chloroacetanilide,
N-(N'-propargylcarbamylmethyl)-2,6-dimethyl-chloroacetanilide,
N-(N',N'-dimethylcarbamylmethyl)-2,6-dimethyl-chloroacetanilide,
N-(n-butoxymethyl)-2,6-diethyl-chloroacetanilide,
N-(2'-n-butoxyethyl)-2,6-diethyl-chloroacetanilide,
N-[3'-methoxybut-(2')-yl]-2,6-dimethylchloroacetanilide,
2-chloro-N-isopropylacetanilide.

Many of the herbicidal chloroacetanilides mentioned above and other herbicidal chloroacetanilides of this type and the production thereof have been described in the aforementioned U.S. Patents and German Offenlegungsschriften.

The antidote of this invention may also be used with herbicidal compositions comprising the above described chloroacetanilides and other herbicidal compounds, e.g. triazine herbicides described in, e.g., U.S. Pat. Nos. 2,891,855 and 2,909,420.

Suitable thiolcarbamates which can be used as herbicides, especially in the case of pretreatment of the seed with the novel oxime ether, are those of the general type:

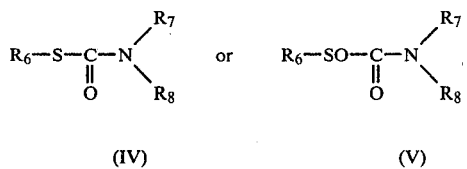

wherein $R_6$ is lower alkyl, alkenyl, chloroallyl, dichloroallyl, trichloroallyl or p-chlorobenzyl, and $R_7$ is lower alkyl having at least 2 carbon atoms, $R_8$ is lower alkyl having at least 2 carbon atoms or cyclohexyl or wherein $R_7$ and $R_8$ together with the nitrogen atom form the hexahydro-1H-azepin ring or the decahydroquinoline or 2-methyl-decahydroquinoline ring.

The following thiolcarbamates may be mentioned as examples of such compounds:

S-ethyl-N,N-dipropylthiocarbamate,
S-ethyl-N,N-diisobutylthiocarbamate,
S-2,3-dichloroallyl-N,N-diisopropylthiolcarbamate,
S-propyl-N-butyl-N-ethylthiolcarbamate,
S-2,3,3-trichloroallyl-N,N-diisopropylthiolcarbamate,
S-propyl-N,N-dipropylthiolcarbamate,
S-ethyl-N-ethyl-N-cyclohexylthiolcarbamate,
S-ethyl-N-hexahydro-1H-azepin-1-carbothioate,
S-isopropyl-N,N-hexamethylen-thiolcarbamate,
S-(p-chlorobenzyl)-N,N-diethylthiolcarbamate,
N-ethylthiocarbonyl-cis-decahydroquinoline,
N-propylthiocarbonyl-decahydroquinaldine,
S-ethyl-N,N-bis(n-butyl)-thiolcarbamate,
S-tert.butyl-N,N-bis(n-propyl)-thiolcarbamate.

Further examples of thiocarbamates that can be used are disclosed by the U.S. Pat Nos. 2,913,327, 3,037,853, 3,175,897, 3,185,720, 3,198,786 and 3,582,314.

The following may be mentioned as further preparations which with the compound of formula I can be made more compatible with the crops of the cultivated plants:

α-[4-(2,4-dichlorophenoxy)-phenoxy]-propionic acid methyl ester,
α-[4-(4-trifluoromethylphenoxy)-phenoxy]-propionic acid methyl ester,
α-[4-(2-chloro-4-trifluoromethylphenoxy)-phenoxy]-propionic acid methyl ester, and
α-[4-(3,5-dichloropyridyl-2-oxy)-phenoxy]-propionic acid methyl ester.

The applied amount of antidote varies between about 0.01 and about 15 parts by weight per part by weight of herbicide. Which ratio with regard to the optimum effect on the specific cultivated plant is most suitable is determined from case to case, i.e. depending on the type of herbicide used.

For the application of the novel compound of formula I for protecting cultivated plants against the attack of agricultural chemicals or, according to another aspect of the invention, for regulating plant growth various methods and techniques are suitable. Such methods and techniques are illustrated by but not limited to the following examples.

(1) Seed dressing (a) Dressing of the seed with the oxime ether of formula I formulated as a wettable powder by shaking of the constituents in a vessel until there exists a uniform distribution over the surface of the seeds (dry dressing). The amount of antidote used for this purpose is about 5 to 500 g (40 g to 2 kg of wettable powder) per 100 kg of seed.

(b) Dressing of the seed with an emulsion concentrate of the oxime ether of formula I by the method and with the amounts given under a) (wet dressing).

(c) Dressing by immersion of the seed in a liquor containing 50–3200 ppm of the compound of formula I for 1–20 hours and subsequent drying of the seed (immersion dressing).

Seed dressing is the preferred mode of use of the antidote compound. There is used as a rule 10 g to 500 g of compound of formula I per 100 kg of seed. The preferred amount of the compound of formula I ranges from about 50 to about 400 grams per 100 kg of seed. Particularly preferred amounts are from 100 to 250 grams per 100 kg of seed, notably from about 150 to about 200 grams per 100 kg of seed, with it being possible, depending on the method used which enables also the addition of other active substances or micronutritients to be made, to deviate either upwards or downwards from the given limiting concentrations (repeat dressings).

(2) Application of tank mixture

A liquid preparation of a mixture an antidote and herbicide (reciprocal quantitive ratio between 10:1 and 1:10) is used, with the applied amount of herbicide being 0.1 to 10 kg per hectare. This tank mixture is preferably applied before emergence (either before or after sowing), or it is worked into the unsown soil to a depth of 5–10 cm.

(3) Application into the seed furrow

The antidote is introduced, as an emulsion concentrate, wettable powder or granulate, into the open sown seed furrows and, after the covering of the seed furrow in the normal manner, the herbicide is applied either before or after emergence of the plants.

The antidote can therefore be applied before, together with, or after the herbicide, and its application to the seeds or to the field before emergence can be effected either before or after sowing; or in certain cases it can be effected also after germination of the seed (post-emergence).

If the antidote is applied simultaneously with the herbicide, this is accomplished by the use of a composition according to the invention, which composition contains the oxime ether of formula I and at least one herbicide e.g. from the chloroacetanilide and/or thiolcarbamate class, together with additives such as carriers and/or distribution agents.

(4) Controlled release of active substance

The active substance in solution is absorbed onto mineral granulate carriers or onto polymerised granulates (urea/formaldehyde), and the material is allowed to dry. It is possible if desired to apply a coating (coated granules), which enables the active substance to be released in controlled amounts over a specific period of time.

(5) Spray solutions

For dipping roots, for spraying upper parts of the plants or for spraying plant parts in general in order to achieve plant growth regulating effects conventionally formulated spray solutions of the compound of formula I can be used.

It is naturally possible to use also all other known methods of applying active substances. Examples in this respect are given further on in the description.

The method according to the invention for the selective control of weeds in cultivated crops, especially of the sorghum and rice genera, is such that the seeds of the cultivated plants or the cultivated areas intended for sowing or already sown, or on which the sown plants have already emerged, are treated, simultaneously, or successively in any desired sequence and at a suitable interval of time, on the one hand with phenylglyoxylonitrile-2-oxime-cyanomethyl ether of formula I as the antidote protecting the cultivated plants or the seed thereof, and on the other hand with at least one herbicidal active substance, e.g. of the chloroacetanilide class and/or of the thiolcarbamate class.

The compositions used, which contain herbicide and antidote separately or together, can be in any suitable conventional form. They can be produced in a manner known per se by the intimate mixing and grinding of the active substance(s) (including antidote) with suitable carriers and/or distributing agents, optionally with the addition of dispersing agents or solvents. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.01 and 90%.

For application, the compound of formula I can be in the following forms (the weight-percentage figures in brackets signify advantageous amounts of active substance):
solid preparations:
dusts and scattering agents (up to 10%), granulates [coated granules, impregnated granules and homogeneous granules] and pellets (1 to 80%);
liquid preparations:

(a) water-dispersible concentrates of active substance: wettable powders and pastes (25 to 90% in the commercial packing, 0.01 to 15% in ready-for-use solutions); emulsion concentrates and solution concentrates 10 to 50%, 0.01 to 15% in ready-for-use solutions);

(b) solutions (0.1 to 20%), e.g. for dressing, aerosols.

The active substance of formula I of the present invention can be formulated for example as follows.

Dust: The following substances are used to produce (a) a 5% dust and (b) a 2% dust:

| | |
|---|---|
| a) | 5 parts of active substance, |
| | 95 parts of talcum; |
| b) | 2 parts of active substance, |
| | 1 part of highly dispersed silicic acid, and |
| | 97 parts of talcum. |

The active substance is mixed and ground with the carriers, and in this form it can be applied by dusting.

Granulate: The following substances are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone; the polyethylene glycol and cetyl polyglycol ether are then added. The solution thus obtained is sprayed onto kaolin, and the acetone is subsequently evaporated off in vacuo. A microgranulate of this kind can be advantageously worked into seed furrows.

Wettable powder: The following constituents are used to produce (a) a 70% wettable powder, (b) a 40% wettable powder, (c) and (d) a 25% wettable powder, and (e) a 10% wettable powder:

| | | |
|---|---|---|
| a) | 70 | parts of active substance, |
| | 5 | parts of sodium dibutylnaphthylsulphonate, |
| | 3 | parts of naphthalenesulphonic acid/phenolsulphonic acid/formaldehye condensate 3:2:1, |
| | 10 | parts of kaolin, and |
| | 12 | parts of Champagne chalk; |
| b) | 40 | parts of active substance, |
| | 5 | parts of sodium lignin sulphonate, |
| | 1 | part of sodium dibutylnaphthalenesulphonate, and |
| | 54 | parts of silicic acid; |
| c) | 25 | parts of active substance, |
| | 4.5 | parts of calcium lignin sulphonate, |
| | 1.9 | parts of Champagne chalk/hydroxyethylcellulose mixture (1:1), |
| | 1.5 | parts of sodium dibutylnaphthalenesulphonate, |
| | 19.5 | parts of silicic acid, |
| | 19.5 | parts of Champagne chalk, and |
| | 28.1 | parts of kaolin; |
| d) | 25 | parts of active substance, |
| | 2.5 | parts of isooctylphenoxy-polyoxyethylene-ethanol, |
| | 1.7 | parts of Champagne chalk/hydroxyethylcellulose mixtue (1:1), |
| | 8.3 | parts of sodium aluminium silicate, |
| | 16.5 | parts of kieselguhr, and |
| | 46 | parts of kaolin; and |
| e) | 10 | parts of active substance, |
| | 3 | parts of a mixture of the sodium salts of saturated fatty alcohol sulphates, |
| | 5 | parts of naphthalenesulphonic acid/formaldehyde condensate, and |

-continued

| | | |
|---|---|---|
| | 82 | parts of kaolin. |

| | | |
|---|---|---|
| a) | 70 | parts of active substance, |
| | 5 | parts of sodium dibutylnaphthylsulphonate, |
| | 3 | parts of naphthalenesulphonic acid/phenolsulphonic acid/formaldehye condensate 3:2:1, |
| | 10 | parts of kaolin, and |
| | 12 | parts of Champagne chalk; |
| b) | 40 | parts of active substance, |
| | 5 | parts of sodium lignin sulphonate, |
| | 1 | part of sodium dibutylnaphthalenesulphonate, and |
| | 54 | parts of silicic acid; |
| c) | 25 | parts of active substance, |
| | 4.5 | parts of calcium lignin sulphonate, |
| | 1.9 | parts of Champagne chalk/hydroxyethylcellulose mixture (1:1), |
| | 1.5 | parts of sodium dibutylnaphthalenesulphonate, |
| | 19.5 | parts of silicic acid, |
| | 19.5 | parts of Champagne chalk, and |
| | 28.1 | parts of kaolin; |
| d) | 25 | parts of active substance, |
| | 2.5 | parts of isooctylphenoxy-polyoxyethylene-ethanol, |
| | 1.7 | parts of Champagne chalk/hydroxyethylcellulose mixtue (1:1), |
| | 8.3 | parts of sodium aluminium silicate, |
| | 16.5 | parts of kieselguhr, and |
| | 46 | parts of kaolin; and |
| e) | 10 | parts of active substance, |
| | 3 | parts of a mixture of the sodium salts of saturated fatty alcohol sulphates, |
| | 5 | parts of naphthalenesulphonic acid/formaldehyde condensate, and |
| | 82 | parts of kaolin. |

The active substance is intimately mixed in suitable mixers with the additives, and the mixture is then ground in the appropriate mills and rollers. There are obtained wettable powders which have excellent wetting and suspension properties, which can be diluted with water to give suspensions of the desired concentration, and which can be used in particular for leaf application, for seed dressing or for the immersion treatment of seedling.

Emulsifiable concentrate: The following substances are used to produce a 25% emulsifiable concentrate:

25 parts of active substance,
2.5 parts of epoxidised vegetable oil,
10 parts of an alkylarylsulphonate/fatty alcohol polyglycol ether mixture,
5 parts of dimethylformamide, and
57.5 parts of xylene.

Emulsions of the desired concentration can be prepared from these concentrates by dilution with water; and these emulsions are particularly suitable for seed dressing.

Example II

Tests with Metolachlor

The following tests were carried out to determine the selective herbicidal action of a highly effective first-class herbicidal compound of the chloroacetanilide class, on its own or together with the antidote of formula I according to the invention. The compound is metolachlor, N-[3'-methoxyprop-(2')-yl]-2-methyl-6 ethyl-chloroacetanilide disclosed in U.S. Pat. No. 3,937,730 and German Offenlegungsschrift No. 2,328,340 of the formula

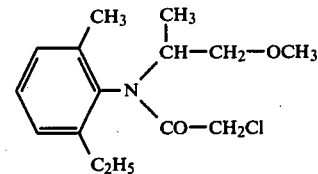

(1) Pre-emergence application as tank mixture (a) After sowing

Aqueous stock liquors (suspensions) from formulated wettable powders of the herbicide (substance II) and the antidote of formula I (substance S) according to the invention were produced. These were then applied, both separately and as mixtures at the given concentrations and in the given mixture ratios, directly after the sowing of various varieties of cultivated millet, namely *Sorghum hybridum* (varieties "Funk", "Dekalb", "NK 222" and "DC 59"), in pots or in seed trays in a greenhouse, the said liquors being applied to the surface of the soil in the sown vessels. The pots or seed trays were then kept at 22°–23° C. with the required amount of watering, and the results were evaluated after 15 days according to the following ratings:

9 = plants undamaged (as in the case of the untreated control plants),
1 = plants completely destroyed,
2–8 = intermediate stages of damage.

(b) Before sowing (PPI)

In the same manner as under a), soil in pots and in seed trays was treated with the liquors containing the active substance, and immediately afterwards these vessels were sown with seed of the millet variety "Funk".

The results are summarised in the following Table I. The concentration values in kg/hectare in relation to the other units of measure are as follows:

1 kg/hectare = 0.1 g/m$^2$ = 2 mg per liter of soil (since seed trays and pots are filled with soil to a depth of 5 cm).

Table I

| Applied concentration in kg/hectare | | Variety of *Sorghum hybridum* | | | | | | | | | | | | | |
|---|---|---|---|---|---|---|---|---|---|---|---|---|---|---|---|
| | | after sowing | | | before sowing | | | | | | | | | | |
| Substance | | Funk b | | | Funk a | | | Dekalb | | | NK222 | | | DC59 | |
| H | S | H | H + S | S | H | H + S | S | H | H + S | S | H | H + S | S | H | H + S | S |
| 2.0 | 4.0 | 1 | 9 | 9 | | | | | | | | | | | | |
| 2.0 | 2.0 | 1 | 9 | 9 | | | | | | | | | | | | |
| 4.0 | 16.0 | | | | 1 | 8 | 9 | 1 | 8 | 9 | 1 | 9 | 9 | 2 | 9 | 9 |
| 4.0 | 8.0 | | | | | 6 | | | 6 | | | 6 | | | 6 | |
| 2.0 | 8.0 | | | | 2 | 9 | 9 | 2 | 8 | 9 | 2 | 9 | 9 | 2 | 9 | 9 |
| 2.0 | 4.0 | | | | | 8 | 9 | | 8 | 9 | | 9 | 9 | | 9 | 9 |

It is seen that the cultivated millet varieties remain virtually unaffected with the application of various mixture ratios H:S at the different concentrations, whereas with application of the herbicide H alone they are completely destroyed even at low concentrations.

(2) Seed dressing (wet)

Aqueous emulsion concentrates (liquid) of the antidote according to the invention were prepared, and the cultivated millet seed (50 g of seed) in a bottle was treated therewith by shaking. The various concentrations of antidote were expressed in grams of antidote per 100 kg of seed. Shortly after this dressing treatment, the seed was sown in pots or in seed trays and then treated in the usual manner, (preemergence) as described under 1)a). The results were evaluated 15 days after application of the herbicide using the same ratings as before; the results are listed in the following Table II.

Table II

| Applied concentration | | Variety of Sorghum hybridum | | | | | | | | | | | |
|---|---|---|---|---|---|---|---|---|---|---|---|---|---|
| Substance S | | Funk | | | Dekalb | | | NK222 | | | DC59 | | |
| g/100 kg of seed | Herbicide H kg/hectare | H | H + S | S | H | H + S | S | H | H + S | S | H | H + S | S |
| 150 | 4 | 1 | 8 | 8 | 1 | 5 | 9 | 1 | 5 | 8 | 3 | 5 | 8 |
| 75 | 4 | | 9 | 9 | | 7 | 9 | | 8 | 9 | | 8 | 9 |
| 37.5 | 4 | | 9 | 9 | | 3 | 9 | | 6 | 9 | | 7 | 9 |
| 150 | 2 | 2 | 9 | | 2 | 8 | | 2 | 8 | | 2 | 8 | |
| 75 | 2 | | 9 | | | 9 | | | 9 | | | 9 | |
| 37.5 | 2 | | 9 | | | 9 | | | 9 | | | 9 | |

The results showed here too that complete protection of the cultivated millet is obtained where the concentration of herbicide H is low, but sufficiently high to combat weeds, even with low applied amounts of the antidote S. With higher doses of herbicide, the results are somewhat different depending on the variety of cultivated millet used; however, in the case of the "Funk" variety, the results are still optimum.

It was possible also in field tests to confirm these excellent results, whereby it was shown that somewhat better results can be obtained with the seed dressing method than with the tank mixture method.

EXAMPLE III

Tests with Metolachlor

Further tests of the antidote compound of formula I (substance S) applied as a seed treatment were carried out, using metolachlor as the herbicide.

Flat pans, 12.7×17.8 cm in dimension, containing field soil (Leon sand, O.M. 2.8%) were planted to sorghum seed (hybrid G-6-22 GBR) and treated as shown in Table III. The seeds were treated and supplied by Funk Seed Company.

Table III

| | | Treatment Rate | | Amt. of Form./ 10 kgs Seed | |
|---|---|---|---|---|---|
| Lot | Treatment | Std. Treatment | Substance S | Std. Treatment | Substance S |
| 1. | Raw Seed | 0 | 0 | 0 | 0 |
| 2. | Substance S | 0 | ½ | 0 | 20 ml. |
| 3. | Substance S | 0 | 1 | 0 | 40 ml. |
| 4. | Substance S | 0 | 2 | 0 | 80 ml. |
| 5. | Std. Treatment | 1.87 | 0 | 18.8 | 0 |
| 6. | Std. Treatment + Substance S | 1.87 | ½ | 18.8 | 20 ml. |
| 7. | Std. Treatment + Substance S | 1.87 | 1 | 18.8 | 40 ml. |
| 8. | Std. Treatment + Substance S | 1.87 | 2 | 18.8 | 80 ml. |
| 9. | Std. Treatment + Substance S | 1.87 | 1 | 18.8 | 40 ml. |

[1]Grams Substance S/kg of seed
[2]Standard seed treatment - Orthocide 75-3 (Chevron Chemical Co.) - 75% captan + 3% methoxychlor
[3]Standard treatment applied, seed dried then applied.
[4]Applied as a pre-treatment mixture, i.e. standard treatment and Substance S were combined and applied as a single treatment.

Metolachlor was applied broadcast preemergence in the equivalent of 467 liters/Ha of water at 1.12, 1.40, 1.68, 1.96, 2.24, 2.52 and 2.80. Each treatment was replicated four times. All plantings received overhead irrigation within 24 hours following treatment. Average high temperatures for the test period was 28° C. and the average low was 21° C. Phytotoxicity ratings and stand counts were made 7, 14, and 21 days after treatment and sorghum plants were clipped, oven dried (48 hours at 72° C.), and weighed at termination of test (21 days) to determine dry weight/replication.

The results of this test are shown in Table IV.

Table IV

| Metolachlor Kg ai/Ha | Seed Lot Number | Sorghum Phytotoxicity[a] | | | Sorghum Stand Count[b] | | | Ave[c] Dry Wt |
|---|---|---|---|---|---|---|---|---|
| | | 7 Day | 14 Day | 21 Day | 7 Day | 14 Day | 21 Day | |
| 0.00 | 1 | 0.0 | 0.0 | 0.0 | 18.00 | 18.25 | 18.25 | 2.95 |
| 1.12 | 1 | 8.0 | 7.0 | 7.0 | 20.00 | 19.25 | 11.25 | 0.47 |
| 1.40 | 1 | 9.0 | 8.0 | 9.0 | 19.00 | 15.50 | 3.75 | 0.11 |
| 1.68 | 1 | 9.0 | 8.0 | 9.0 | 16.25 | 15.00 | 5.25 | 0.20 |
| 1.96 | 1 | 9.0 | 8.0 | 9.5 | 17.75 | 17.25 | 2.25 | 0.05 |
| 2.24 | 1 | 9.0 | 8.0 | 9.0 | 19.25 | 18.50 | 2.75 | 0.08 |
| 2.52 | 1 | 9.0 | 8.0 | 9.5 | 18.75 | 12.25 | 0.75 | 0.03 |
| 2.80 | 1 | 9.0 | 9.0 | 9.5 | 19.00 | 16.75 | 1.50 | 0.04 |
| 0.00 | 2 | 0.0 | 0.0 | 0.0 | 18.50 | 18.25 | 18.50 | 3.47 |
| 1.12 | 2 | 7.0 | 5.0 | 3.0 | 18.00 | 18.75 | 15.50 | 1.43 |
| 1.40 | 2 | 7.0 | 5.0 | 3.0 | 18.75 | 17.50 | 14.75 | 1.45 |
| 1.68 | 2 | 7.5 | 4.0 | 3.0 | 17.75 | 18.25 | 15.50 | 1.14 |
| 1.96 | 2 | 7.5 | 6.0 | 4.0 | 19.25 | 16.25 | 13.00 | 1.06 |
| 2.24 | 2 | 8.0 | 7.0 | 6.0 | 19.25 | 16.00 | 8.75 | 0.59 |
| 2.52 | 2 | 8.0 | 7.0 | 6.0 | 18.75 | 15.00 | 8.50 | 0.51 |

Table IV-continued

| Metolachlor Kg ai/Ha | Seed Lot Number | Sorghum Phytotoxicity[a] | | | Sorghum Stand Count[b] | | | Ave[c] Dry Wt |
|---|---|---|---|---|---|---|---|---|
| | | 7 Day | 14 Day | 21 Day | 7 Day | 14 Day | 21 Day | |
| 2.80 | 2 | 8.5 | 7.0 | 7.0 | 18.25 | 16.25 | 10.50 | 0.43 |
| 0.00 | 3 | 0.0 | 0.0 | 0.0 | 17.75 | 18.00 | 17.50 | 2.98 |
| 1.12 | 3 | 3.5 | 4.0 | 2.0 | 17.00 | 17.75 | 17.50 | 1.88 |
| 1.40 | 3 | 3.5 | 3.0 | 1.0 | 18.75 | 19.00 | 17.25 | 2.16 |
| 1.68 | 3 | 4.0 | 3.0 | 1.0 | 18.50 | 18.50 | 18.50 | 1.97 |
| 1.96 | 3 | 4.0 | 4.0 | 2.0 | 17.75 | 17.50 | 16.75 | 1.53 |
| 2.24 | 3 | 7.0 | 5.0 | 3.0 | 17.25 | 16.75 | 14.50 | 1.38 |
| 2.52 | 3 | 7.0 | 6.0 | 3.0 | 18.25 | 18.00 | 16.50 | 1.44 |
| 2.80 | 3 | 8.0 | 6.0 | 4.0 | 18.75 | 18.50 | 14.75 | 0.96 |
| 0.00 | 4 | 0.0 | 0.0 | 0.0 | 19.00 | 19.00 | 19.00 | 2.53 |
| 1.12 | 4 | 2.0 | 0.0 | 0.0 | 17.25 | 17.75 | 17.50 | 2.27 |
| 1.40 | 4 | 0.0 | 0.0 | 0.0 | 18.25 | 18.75 | 18.50 | 2.07 |
| 1.68 | 4 | 3.0 | 2.0 | 0.0 | 17.00 | 17.25 | 17.00 | 2.16 |
| 1.96 | 4 | 3.0 | 3.0 | 0.0 | 15.75 | 16.50 | 16.50 | 2.37 |
| 2.24 | 4 | 5.0 | 4.0 | 2.0 | 16.30 | 17.00 | 16.25 | 1.59 |
| 2.52 | 4 | 4.5 | 4.0 | 1.0 | 16.00 | 16.00 | 15.50 | 1.59 |
| 2.80 | 4 | 5.0 | 5.0 | 0.0 | 15.00 | 16.50 | 15.00 | 1.62 |
| 0.00 | 5 | 0.0 | 0.0 | 0.0 | 18.75 | 19.25 | 19.00 | 3.34 |
| 1.12 | 5 | 7.0 | 7.0 | 6.0 | 18.75 | 16.75 | 10.50 | 0.46 |
| 1.40 | 5 | 8.0 | 8.0 | 8.0 | 18.25 | 15.50 | 3.75 | 0.16 |
| 1.68 | 5 | 8.0 | 8.0 | 8.0 | 18.00 | 16.75 | 4.75 | 0.16 |
| 1.96 | 5 | 8.0 | 8.0 | 8.0 | 18.50 | 15.50 | 3.75 | 0.17 |
| 2.24 | 5 | 9.0 | 8.0 | 9.0 | 17.50 | 16.25 | 6.25 | 0.15 |
| 2.52 | 5 | 9.0 | 9.0 | 9.8 | 18.00 | 10.25 | 0.75 | 0.02 |
| 2.80 | 5 | 9.0 | 8.0 | 8.0 | 17.50 | 16.00 | 4.00 | 0.18 |
| 0.00 | 6 | 0.0 | 0.0 | 0.0 | 17.75 | 18.75 | 17.75 | 2.66 |
| 1.12 | 6 | 3.5 | 3.0 | 4.0 | 18.75 | 18.75 | 17.25 | 1.48 |
| 1.40 | 6 | 4.0 | 4.0 | 2.0 | 16.50 | 16.75 | 16.25 | 1.76 |
| 1.68 | 6 | 4.0 | 5.0 | 2.0 | 18.50 | 18.50 | 18.00 | 1.66 |
| 1.96 | 6 | 5.0 | 5.0 | 2.0 | 18.00 | 17.75 | 16.75 | 1.37 |
| 2.24 | 6 | 6.0 | 5.0 | 5.0 | 18.25 | 18.50 | 17.25 | 0.93 |
| 2.52 | 6 | 6.0 | 6.0 | 4.0 | 18.00 | 15.25 | 11.75 | 0.89 |
| 2.80 | 6 | 6.0 | 5.0 | 4.0 | 19.00 | 18.25 | 13.75 | 0.99 |
| 0.00 | 7 | 0.0 | 0.0 | 0.0 | 18.75 | 19.25 | 19.00 | 2.49 |
| 1.12 | 7 | 3.0 | 3.0 | 3.5 | 19.50 | 18.75 | 18.25 | 1.60 |
| 1.40 | 7 | 3.5 | 3.0 | 1.0 | 17.75 | 18.25 | 17.50 | 2.02 |
| 1.68 | 7 | 3.5 | 4.0 | 2.0 | 19.00 | 18.25 | 17.75 | 1.66 |
| 1.96 | 7 | 3.5 | 3.0 | 1.0 | 19.00 | 19.25 | 17.50 | 2.11 |
| 2.24 | 7 | 4.0 | 4.0 | 2.0 | 18.25 | 18.25 | 17.00 | 1.75 |
| 2.52 | 7 | 4.0 | 4.0 | 2.0 | 19.25 | 19.50 | 18.00 | 1.76 |
| 2.80 | 7 | 4.0 | 4.0 | 3.0 | 19.00 | 19.00 | 16.75 | 1.44 |
| 0.00 | 8 | 0.0 | 0.0 | 0.0 | 17.75 | 18.50 | 17.75 | 2.81 |
| 1.12 | 8 | 1.0 | 0.0 | 0.0 | 18.70 | 19.25 | 18.75 | 2.33 |
| 1.40 | 8 | 1.0 | 0.0 | 0.0 | 17.75 | 18.50 | 17.50 | 2.45 |
| 1.68 | 8 | 1.0 | 2.0 | 0.0 | 18.50 | 18.75 | 19.25 | 2.19 |
| 1.96 | 8 | 2.0 | 2.0 | 1.0 | 17.25 | 18.75 | 17.25 | 2.04 |
| 2.24 | 8 | 2.0 | 2.0 | 1.0 | 18.00 | 18.00 | 18.00 | 1.94 |
| 2.52 | 8 | 3.5 | 4.0 | 1.0 | 18.50 | 18.25 | 16.75 | 1.77 |
| 2.80 | 8 | 4.0 | 3.0 | 3.0 | 17.50 | 18.50 | 17.00 | 1.68 |
| 0.00 | 9 | 0.0 | 0.0 | 0.0 | 18.75 | 18.75 | 18.50 | 2.85 |
| 1.12 | 9 | 3.0 | 1.0 | 0.0 | 18.50 | 18.75 | 18.75 | 2.15 |
| 1.40 | 9 | 3.0 | 3.0 | 0.0 | 18.75 | 18.00 | 17.50 | 2.30 |
| 1.68 | 9 | 3.0 | 3.0 | 5.0 | 19.00 | 18.75 | 18.50 | 1.87 |
| 1.96 | 9 | 4.0 | 5.0 | 3.0 | 18.25 | 17.00 | 14.00 | 1.50 |
| 2.24 | 9 | 4.0 | 5.0 | 4.0 | 18.25 | 17.50 | 14.25 | 1.11 |
| 2.52 | 9 | 6.0 | 6.0 | 5.0 | 18.25 | 16.50 | 12.75 | 1.10 |
| 2.80 | 9 | 7.0 | 6.0 | 6.0 | 16.25 | 14.25 | 10.25 | 0.64 |

[a]Zero equals no effect and ten equals complete control.
[b]Average/replication number of plants emerged (20 seeds planted/replication).
[c]Average dry weight/replication expressed in grams.

The addition of Substance S as a seed treatment at all rates safened (decreased phytotoxicity, and increased seed count) sorghum seedlings against damage by metolachlor at all tested herbicide rates. The greatest degree of safening existed in seed lots 4 and 8 which received 2.0 gm Substance S kg seed. Seed lot 4 did not receive the standard fungicide and insecticide treatment whereas seed lot 8 did receive this treatment. Table IV shows the phytotoxicity ratings and stand counts for the various seed lots at 7, 14, and 21 days after treatment and the average dry weight at 21 days. One of the most notable points from this table is the lack of reduction in stand count at the 7 and 14 day ratings Phytotoxicity at these early ratings when no safener was present was high. However, the seedlings were still able to emerge. At the 21 day rating, the stand count in the seed samples with low levels of safener or without safener all had decreased significantly because the affected plants had all died by this later date. With seed lot 5 and 2.80 kg ai/kg metolachlor, dry weight per replication was only 0.18 g whereas the average for seed lot 8, this weight was 1.68. This comparison shows the significant effect the safener has on herbicide activity.

Combinations of metolachlor or other chloroacetanilides with certain triazine herbicides, including ametryn (2-ethylamino-4-isopropylamino-6-methylthio-s-triazine), atrazine (2-chloro-4-ethylamino-6-isopropylamino-s-triazine), prometryn [2,4-bis(isopropylamino)-6-methylthio-s-triazine], propazine [2- chloro-4,6-bis (isopropylamino)-s-triazine], simazine [2-chloro-4,6-bis(ethylamino)-s-triazine], terbuthylazine (2-tert.butylamino-4-chloro-6-ethylamino-s-triazine) and terbutryn (2-tert.butylamino-4-ethylamino-6-methylthio-s-triazine), are excellent for the control of weeds in crop cultures. The use of the antidote of formula I permits those combination herbicides-particularly metolachlor in combination with atrazine, propazine, terbuthylazine and terbutryn to be used safely in various crops such as sorghum.

EXAMPLE IV

Tests with other chloroacetanilides

The efficacy of the antidote of formula I was tested for its safening effect in conjunction with chloroacetanilides other than metolachlor. The chloroacetanilides tested were:

Substance A—N-(2'-methoxyethyl)-2,6-dimethylchloroacetanilide
Substance B—N-[3'-methoxyprop-(2')-yl]-2,6-dimethylchloroacetanilide
Substance C—N-[2'-methoxyprop-(1')-yl]-2,6-dimethylchloroacetanilide
Substance D—N-[2'-methoxyprop-(1')-yl]-2-methyl-6-ethyl-chloroacetanilide
Substance E—N-[3'-ethoxyprop-(2')-yl]-2methyl-6-ethyl-chloroacetanilide
Substance F—N-(2'-ethoxyethyl)-2-fluoro-chloroacetanilide
Substance G—N-[3'ethoxyprop-(2')-yl]-2-fluoro-chloroacetanilide
Substance J—N-[3'-methoxybut-(2')-yl]-2,6-dimethylchloroacetanilide
Substance L—N-methoxymethyl-2,6-diethyl-dichloroacetanilide (alachlor)

*Sorghum hybridum* seed (variety "Funk") and Möhlin-type soil were employed. Tests were run as (1) pre-emergent application of a tank mixture of herbicide and safener and (2) seed dressing. Both types of tests were performed according to the manner of Example II.

For the tank mixture, the dosage rates were, per part of herbicide, 4 parts, 2 parts and 1 part safener. For the seed dressing, the dosage rates were 37.5, 75 and 150 grams of antidote compound (Substance S) per 100 kg of seed.

The results are shown in Table V, where the rating scale used is that of Example II.

Table V

| Herbicide | | Ratings | | | Seed Dressing | | |
|---|---|---|---|---|---|---|---|
| Substance | kg/Ha | Herbicide alone | Tank Mixture 1:4 | 1:2 | 1:1 | 150 gms | 75 gms | 37.5 gms |
| A | 2 | 1 | 2 | 2 | — | — | 4 | 2 |
| B | 2 | 1 | 5 | 5 | — | — | 8 | 6 |
| C | 4 | 2 | 2 | 2 | — | 6 | 3 | 2 |
| D | 4 | 2 | 3 | 2 | — | 6 | 5 | 5 |
| E | 4 | 2 | 4 | 4 | — | 7 | 6 | 6 |
| F | 4 | 3 | 6 | 6 | — | 8 | 9 | 9 |
| G | 4 | 2 | 5 | 5 | — | 7 | 6 | 3 |
| J | 4 | 2 | 7 | 4 | — | 9 | 8 | 7 |
| L | 4 | 2 | 7 | 6 | 4 | — | 9 | 8 |

These data show that the antidote compound of formula I is effective as a safener in conjunction with a broad range of chloroacetanilide herbicides.

EXAMPLE V

Tests with other herbicides

The efficacy of the antidote of formula I was tested for its safening effect in conjunction with herbicides other than chloroacetanilides. The herbicides tested were:

Substance M—S-ethyl-N,N-diisobutylthiocarbamate (butylate)
Substance N—2-chloro-N-isopropylacetanilide (propachlor)

Test methods were the same as in Example IV.
The results are shown in Table VI.

Table VI

| Herbicide | | Ratings | | | Seed Dressing | |
|---|---|---|---|---|---|---|
| Substance | kg/Ha | Herbicide alone | Tank Mixture 1:4 | 1:2 | 1:1 | 75 gms | 37.5 gms |
| M | 4 | 3 | 4 | 4 | 5 | 8 | 7 |
| N | 16 | 6 | 7 | 7 | 8 | 9 | 9 |

The antagonistic action of the antidote according to the invention does not extend to the principal weeds normally associated with cultivated plants, e.g. Echinochloa, *Setaria italica, Digitaria sanguinalis*, etc. These weeds are destroyed by the herbicides used with the antidote practically to the same high degree as that resulting without the presence of the antidote.

Also insecticides, fungicides, etc., such as Diazinon, captan, methoxychlor and so forth, do not lose their effectiveness as a result of the antidote; such insecticides can therefore be concomitantly used in seed dressing.

EXAMPLE VI

Safening in rice crops

Good "safening" effects similar to those resulting with the use of the herbicide II can be obtained when the oxime ether according to the invention is employed with thiolcarbamates and with other chloroacetanilides even on other crops, as is shown by the following test with rice where N-[2'-n-propoxyethyl]-2,6-diethyl-chloroacetanilide of the formula

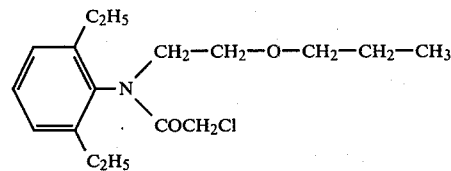

is used as the herbicide (K).

Rice is grown in very moist soil until the plants are carrying 3 to 4 leaves. The plants are then taken from the soil and the adhering soil is washed from the roots with water. The roots are thereupon immersed for 30 minutes in aqueous preparations containing respectively 125, 32, 8 and 2 ppm (=parts of active substance per 10$^6$ parts of the "solution") of the antidote, phenyl-glyoxylonitrile-2-oximecyanomethyl ether.

The rice plants treated in this manner are then planted in soil in containers having a surface area of 12 cm × 8 cm and a depth of 15 cm (96 cm$^2$ surface area and 1.44 liters volume per container). The height of water is subsequently adjusted to 2 cm. Spraying is carried out after 10 days with a 0.4% liquor of the herbicide K [N-(2'-n-propyloxyethyl)-2,6-diethyl-N-chloroacetanilide], the equivalent amount of liquor being 500 liters per hectare or 2 kg/hectare (=0.5 cm³ of liquor per container). The liquor is sprayed over the leaves of the rice plants and into the water. The test is evaluated 20 days after the treatment with the herbici. Evaluation is on the basis of the scale of ratings used in the test with millet (9=normal condition; 1=completely destroyed).

The results are summarized in the following table:

Table VII

| Conc. herbicide K | Conc. antidote S | Toxicities on rice K (alone) | K + S | S (alone) |
|---|---|---|---|---|
| 2 kg/ha | 125 ppm | 4 | 8 | 9 |
| 2 kg/ha | 32 ppm | 4 | 7 | 9 |
| 2 kg/ha | 8 ppm | 4 | 8 | 9 |
| 2 kg/ha | 2 ppm | 4 | 8 | 9 |

EXAMPLE VII

Biological tests under stress conditions

Plant growth at below optimum temperature

Rice plants in the 2- to 3-leaf stage were immersed with the roots and the lower part of the shoot for 45 minutes in a solution containing 10 ppm (=0.001%) of active substance of formula I. They were afterwards replanted in dripping wet soil in asbestos cement containers 70×70 cm in size, and kept at a temperature of only 18°–22° C. instead of at 28°–30° C. The surface of the soil in the containers was covered with 2–3 cm of water after 3 days. After a further 18 days, the treated plants were compared with the untreated control plants.

The rice plants treated with the compounds of formula I had a root system which was on average 30 to 50% larger. Compounds of the U.S. Pat. No. 3,799,757 showed no such action.

In addition to the above described activities of the compound of formula I according to the invention, there is observed a certain antagonising counteraction on the growth-inhibiting effect of some growth regulators on grasses in the case of overdosage of the growth inhibitor. Furthermore, the compound of formula I, used on its own exhibits a germination-stimulating action on certain seed varieties such as those of sorghum, rice etc.

What is claimed is:

1. A method for promoting the germination of seed of cultivated plants, wherein the seed is treated, before or during germination, with an effective amount of phenylglyoxylonitrile-2-oxime-cyanomethyl ether.

2. A method according to claim 1, in which the cultivated plant is sorghum.

3. A method according to claim 1, in which the cultivated plant is rice.

4. A method for promoting the growth of the root system of cultivated plants, wherein the roots of such plants are treated with an effective amount of phenylglyoxylonitrile-2-oxime-cyanomethyl ether.

5. A method according to claim 4 in which the cultivated plant is rice.

* * * * *